US00PP21161P2

(12) United States Plant Patent
Ichie

(10) Patent No.: US PP21,161 P2
(45) Date of Patent: Jul. 13, 2010

(54) ***HYDRANGEA* PLANT NAMED 'FANFARE'**

(50) Latin Name: *Hydrangea macrophylla*
Varietal Denomination: Fanfare

(76) Inventor: Toyokazu Ichie, 3-46 Hongou, Kakegawa-city, Shizuoka (JP) 436-0111

( * ) Notice: Subject to any disclaimer, the term of this patent is extended or adjusted under 35 U.S.C. 154(b) by 0 days.

(21) Appl. No.: 12/386,151

(22) Filed: Apr. 14, 2009

(51) Int. Cl.
*A01H 5/00* (2006.01)

(52) U.S. Cl. ..... Plt./250

(58) Field of Classification Search ..... Plt./250
See application file for complete search history.

*Primary Examiner*—Annette H Para
(74) *Attorney, Agent, or Firm*—Penny J. Aguirre

(57) ABSTRACT

A new cultivar of *Hydrangea macrophylla* named 'Fanfare' that is characterized by its ability to re-bloom on new growth after deadheading, its consistently formed rounded, hortensia type inflorescences with sepals that are round to broadly elliptic in shape and blue in color with white to pale pink margins when grown under acidic soil conditions and pink in color with white margins when grown under alkaline soil conditions, its compact growth habit with strong stems that enable pot culture without the need for staking, its dark green glossy foliage and its hardiness at least in U.S.D.A. Zones 5 to 9.

2 Drawing Sheets

Botanical classification: *Hydrangea macrophylla.*
Varietal denomination: 'Fanfare'.

BACKGROUND OF THE INVENTION

The present invention relates to a new and distinct cultivar of *Hydrangea macrophylla* and will be referred to hereafter by its cultivar name, 'Fanfare'. 'Fanfare' represents a new mophead type bigleaf hydrangea, a deciduous shrub grown for landscape use and for use as a potted plant.

'Fanfare' was derived from an ongoing controlled breeding program in a nursery that focuses on new cultivars of bigleaf hydrangeas for container and landscape use. 'Fanfare' originated from a cross made in the Inventor's nursery in June 1999 in Shizuoka, Japan between an unpatented proprietary selection of *Hydrangea macrophylla* designated as H3-67 as the female and *Hydrangea macrophylla* 'Alexsandria' (not patented) as the male parent. The new *Hydrangea* was selected as a unique single plant from the progeny of the cross in March 2006.

Asexual reproduction of the new cultivar was first accomplished by softwood stem cuttings by the Inventor in Shizuoka, Japan in May 2007. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Fanfare' as a unique cultivar of *Hydrangea macrophylla.*

1. 'Fanfare' is a strong bloomer and exhibits a re-blooming habit with inflorescences produced from early summer until fall with removal of spent blooms; observed in Shizuoka, Japan, Niagara on the Lake, Ontario, Canada, and Warsaw, N.C.
2. 'Fanfare' exhibits consistently formed hortensia type inflorescences that are rounded in shape.

3. The sterile flowers of 'Fanfare' exhibit sepals that are round to broadly elliptic in shape with marginal variegation; blue in color with white to pale pink margins when grown under acidic soil conditions and pink in color with white margins when grown under alkaline soil conditions.
4. 'Fanfare' exhibits a compact growth habit with strong stems that enable pot culture without the need for staking.
5. 'Fanfare' exhibits dark green glossy foliage.
6. 'Fanfare' is hardy at least to U.S.D.A. Zones 5 to 9.

The new cultivar of *Hydrangea* differs from its parents, H3-67 and 'Alexsandria', in having sterile flowers with sepals that exhibit marginal variegation whereas the sepals of the parent plants are non-variegated. 'Fanfare' can be most closely compared to the cultivar 'Harlequin' (not patented) which also exhibits sterile flowers with white variegated sepal margins and in having similar foliage characteristics. 'Harlequin' differs from 'Fanfare' in having sterile flowers sepals that are deep pink in color with white margins and also differs in blooming on old wood and lacking a reblooming habit.

BRIEF DESCRIPTION OF THE DRAWINGS

The accompanying colored photographs illustrate the overall appearance and distinct characteristics of the new*Hydrangea*.

The photographs were taken of three year-old plants of 'Fanfare' as grown outdoors in three-gallon containers in Shizuoka, Japan.

Figure 1:
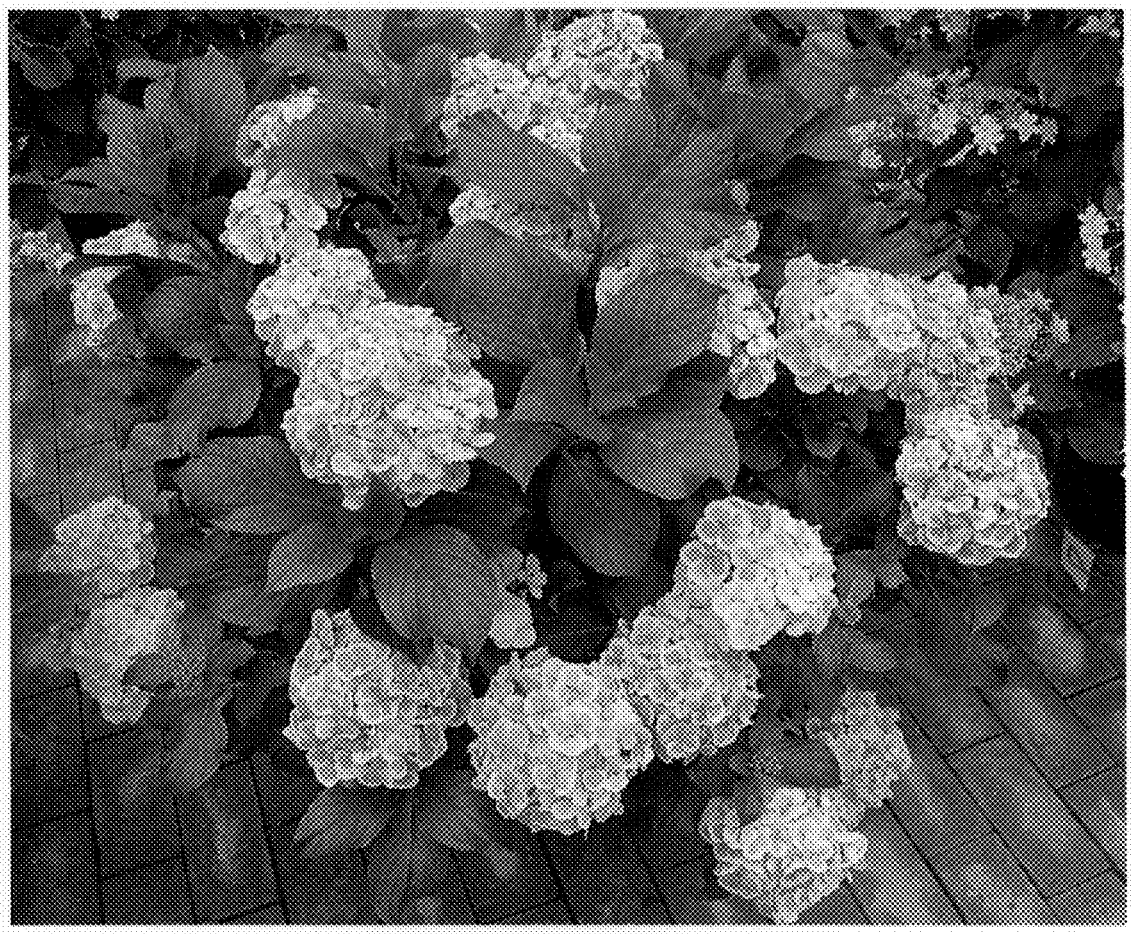

The photograph in FIG. 1 illustrates the foliage, flowering habit and plant habit as observed when grown under acidic soil conditions.

Figure 2:
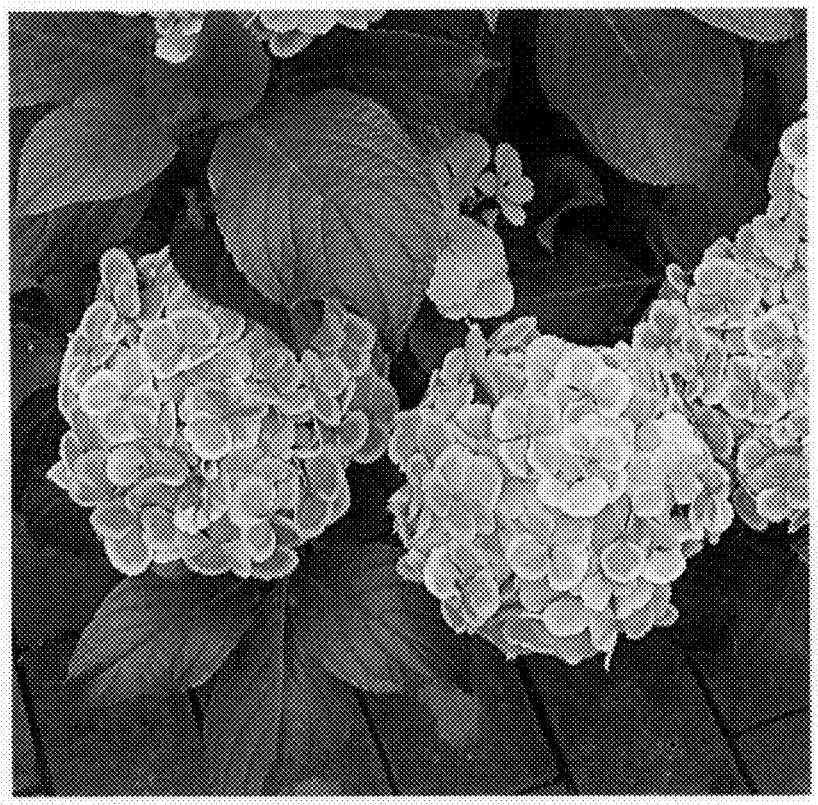

The photograph in FIG. 2 illustrates a close-up view of inflorescences of 'Fanfare' as grown under acidic soil conditions.

Figure 3:
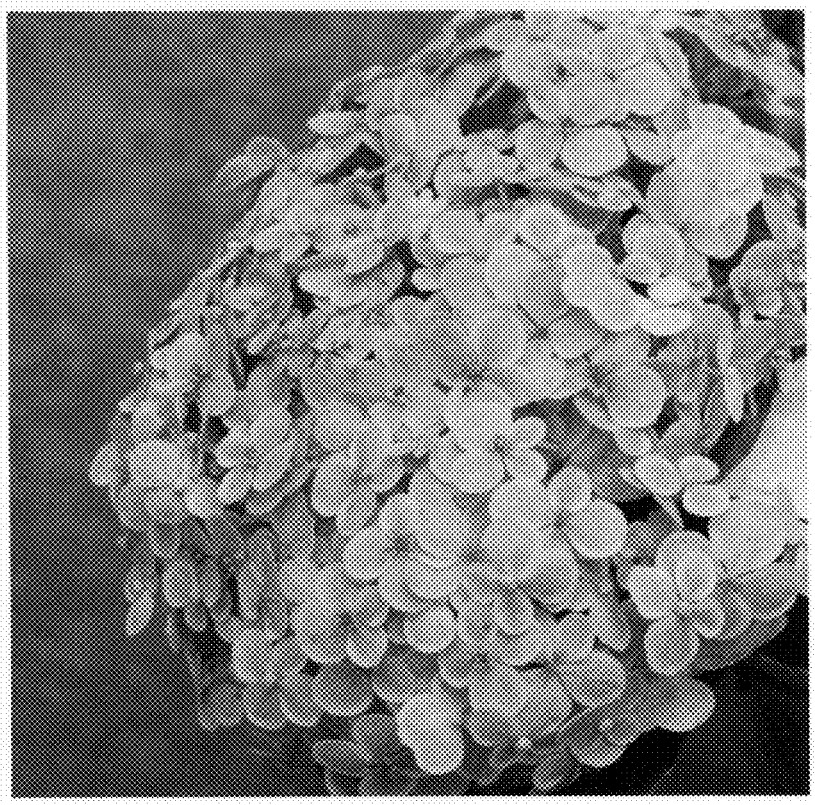

The photograph in FIG. 3 illustrates a close-up view of inflorescences of 'Fanfare' as grown under alkaline soil conditions.

The colors in the photographs may differ slightly from the color values cited in the detailed botanical description, which accurately describe the colors of the new *Hydrangea*.

BOTANICAL DESCRIPTION OF THE PLANT

The following is a detailed description of a three year-old plants of 'Fanfare' as grown outdoors in three-gallon container in Shizuoka, Japan. The detailed data was taken from plants growing under alkaline conditions with color data provided for the flowers of plants grown under acidic condition were differences exist. Phenotypic differences may be observed with variations in environmental, climatic, and cultural conditions. The color determination is in accordance with the 2007 R.H.S. Colour Chart of The Royal Horticultural Society, London, England, except where general color terms of ordinary dictionary significance are used.

General description:

*Blooming period.*—Reblooming from June until fall from with removal of spent blooms in Shizuoka, Japan, Niagara on the Lake, Ontario, Canada, and Warsaw, N.C.

*Plant habit.*—Broadly upright, compact, deciduous shrub.

*Height and spread.*—Reaches about 60 cm in height and width on three-year-old plants in a 3-gallon container.

*Hardiness.*—At least to U.S.D.A. Zones 5 to 9.

*Diseases resistance.*—No susceptibility or resistance to diseases has been observed.

*Root description.*—Fine.

Growth and propagation:

*Propagation.*—Softwood stem cuttings.

*Growth rate.*—Moderate.

Stem description:

*Stem shape..*—Round, solid.

*Stem strength.*—Strong.

*Stem color.*—New growth; 144A to 144B with lenticels 165A, woody; 162C to 162D.

*Stem size.*—Up to 70 cm (including peduncle) in length, average of 6.3 cm in width.

*Stem surface.*—Glabrous, satiny, sparsely covered with lenticels; about 12 per square cm, about 1.5 mm in length and 0.7 mm width, stem becomes bark-like with age.

*Branching.*—Lateral branching is determined by pinching; 2 stems develop per pinched node.

Foliage description:

*Leaf shape.*—Ovate to broadly elliptic.

*Leaf arrangement.*—Opposite.

*Leaf division.*—Simple.

*Leaf base.*—Cuneate.

*Leaf apex.*—Cuspidate.

*Leaf margins.*—Crenate, average of 19 per side on a leaf 11 cm in length.

*Leaf venation.*—Pinnate, recessed on upper surface and raised on lower surface, color 144B to 144D on upper surface and lower surface.

*Leaf size.*—Average of 15 cm in length and 9 cm in width.

*Internode length.*—Average of 5 cm.

*Leaf attachment.*—Petiolate.

*Leaf surface.*—Glabrous and glossy on upper surface, dull and very finely puberulent on lower surface.

*Leaf color.*—Upper surface; N137C, lower surface; 138A to 138B.

*Petioles.*—Average of 3 cm in length and 5 mm in width, 145A in color, glabrous surface.

Inflorescence description:

*Inflorescence type.*—Hortensia type (mophead); terminal compound globose corymbs comprised of rotate shaped sterile flowers and some fertile flowers, the eye of the sterile flowers is either closed or pistillate.

*Inflorescence shape.*—Hemispherical.

*Lastingness of inflorescence.*—Persistent. Lasting up to 5 months.

*Inflorescence number.*—One per lateral stem.

*Inflorescence size.*—Average of 8.5 cm in depth and 17 cm in diameter.

*Flower number.*—Average of 220 sterile flowers and 15 fertile flowers.

*Flower fragrance.*—None.

*Inflorescence aspect.*—Upright at stem terminus.

*Flower size.*—Sterile flowers; up to 3 cm in diameter and 1.5 mm in depth, fertile flowers; average of 4 mm in diameter and 8 mm in depth.

*Flower buds.*—Sterile flowers; average of 4 mm in length, and 3 mm in width prior to opening, ovate in shape, 75A to 75C in color (alkaline conditions) or 97A to 97C (acidic conditions), fertile flowers; average of 1.5 mm in width and diameter, globose in shape, 145D blended with 75C in color (alkaline conditions) and 145D blended with 97C (acid conditions).

*Peduncles.*—Average of 1.5 cm in length and 1.8 mm in width on individual corymbs, color 145D blended with 75A (alkaline conditions) or blended with 97C (acid conditions), glabrous surface.

*Pedicels.*—Sterile flowers; average of 1 cm in length and 1.3 mm in width, color 75A, fertile flowers; 5 mm in length and 1.2 mm in width, 75A blended with 145C in color (alkaline conditions) or 97B blended with 145C (acidic conditions), surface is glabrous on all flowers.

*Petals.*—Sterile flowers; 5, quickly shed, rotate in arrangement, ovate in shape, entire margin, acute apex, truncate base, average of 1.5 mm in length and mm in width, surface is glabrous and dull on both surfaces, color of upper and lower surface N155C to 75D (alkaline conditions) or N155C to 97D (acid conditions), fertile flowers; 5, 4 are loosely orbicular (about 1 mm in length and width) and one is larger and ovate in shape (about 3 mm in length and 2 mm in width), 145C in color tinted with 75C (alkaline conditions) or 145C tinted with 97C (acid conditions), rounded apex, truncate base, glabrous surface.

*Sepals.*—Sterile flowers only; 4 (occasionally 5), orbicular to broadly elliptic in shape, average of 1 cm in length and 9 mm in width, rounded to broadly acute apex, cuneate base, glabrous surface on upper and lower surface, held nearly flat, entire margin, color when grown under alkaline conditions: upper surface; blend of 75A and 75B with veins 77B with a margin about 1 mm in width of 155D, color of lower surface; 155D with veins 77A and margin about 1 mm in width and 155D, both surfaces become suffused with 145C as they age, eye; 75D in color if closed (some are pistillate with petals), color when grown under acidic conditions: upper surface; blend of 97A to 97C with some suffused with 85A with veins 97A with a margin about 1 mm in width of 155D to 69D, color of lower surface; 155D With veins 97A and margin about 1 mm in width and 155D to 69D, both surfaces become suffused with 145C as they age, eye; 97A to 97B in color if closed (some are pistillate with petals), Reproductive organs: (fertile flowers; perfect, sterile flowers; can be pistillate).

*Stamens.*—Average of 8, anther has 2 renal-shape sections, about 0.7 mm in length and about 77A in color, filament is an average of 1.5 mm in length and 77A in color (alkaline conditions) or 94B (acid conditions), pollen is abundant and 11C in color.

*Pistils.*—2 to 3, average of 1.2 mm in length and 0.5 mm in width, club-shaped, stigma is 199A in color, style is an average of 1 mm in length and 77B to 77C in color (alkaline conditions) or 94B to 94D (acid conditions).

*Fruit and seed.*—Has not been observed under the conditions tested to date.

It is claimed:

1. A new and distinct cultivar of *Hydrangea* plant named 'Fanfare' substantially as herein illustrated and described.

* * * * *